(12) United States Patent
Van Hale

(10) Patent No.: US 7,037,110 B1
(45) Date of Patent: May 2, 2006

(54) PROTECTIVE BARRIER

(76) Inventor: Gregory Van Hale, 247 W. Glenoaks Blvd., Glendale, CA (US) 91202

( * ) Notice: Subject to any disclaimer, the term of this patent is extended or adjusted under 35 U.S.C. 154(b) by 0 days.

(21) Appl. No.: 10/906,736

(22) Filed: Mar. 3, 2005

(51) Int. Cl.
*A61C 1/16* (2006.01)

(52) U.S. Cl. ...................................... 433/116; 600/121

(58) Field of Classification Search ................ 433/116; 600/121, 122, 124, 125, 123
See application file for complete search history.

(56) References Cited

U.S. PATENT DOCUMENTS

| | | | |
|---|---|---|---|
| 1,539,253 A * | 5/1925 | Fuller | 433/116 |
| 5,490,781 A * | 2/1996 | Wade | 433/116 |
| 6,273,716 B1 * | 8/2001 | Wade | 433/116 |
| 6,350,124 B1 * | 2/2002 | Wade | 433/116 |

* cited by examiner

*Primary Examiner*—Cary E. O'Connor
(74) *Attorney, Agent, or Firm*—James E. Brunton, Esq.

(57) ABSTRACT

A protective barrier that can be removably fitted over a dental instrument to protect against the transfer of contaminants from one dental patient to another via the dental instrument. The protective barrier, when in use will generally replicate the ergonomic features found on the outer surface of the dental instrument. The barrier is constructed from two mating half portions that include interior chambers and are adapted for placement over and in proximate contact with at least a portion of the outer surface of a dental instrument. The interior chambers of each half portion uniquely contain a yieldably deformable cushion-like elastomer such as polyurethane foam.

20 Claims, 6 Drawing Sheets

PROTECTIVE BARRIER

BACKGROUND OF THE INVENTION

1. Field of the Invention

The present invention relates to protective barriers. More particularly, the invention relates to protective barriers for use with dental instruments and like devices to prevent the spread of contaminants.

It has long been recognized in the dental industry that after an infectious agent from one patient contaminates a dental instrument, the instrument has the potential to spread the contaminants to the next patient unless special care is taken to replace the instrument or properly sterilize it. As a general rule, replacing the instrument parts which are vulnerable to contamination is prohibitively expensive and sterilizing the parts by autoclaving is time consuming. While attempts have been made in the past to sterilize the instrument parts by spraying the parts with a disinfectant, experience has shown that such an approach is inadequate to effectively remove all contaminants.

2. Discussion of the Prior Art

In the past, various attempts have been made to provide protective plastic sheaths of various configurations for covering hand held dental tools. For example, U.S. Pat. No. 5,921,776, issued to Heilbrunn, discloses a barrier device that includes a disposable sheath, which can be positioned to shroud the instrument without encumbering its functionality. The device further includes a disposable probe which is integrally formed with the sheath and which is attached to the instrument along with the sheath.

In a similar vein, U.S. Pat. No. 4,907,968 issued to Eisner, et al., discloses a yieldably deformable shield or prophylactic, which exhibits sufficient deformability to adapt to any of a variety of angular or curved shapes of the nozzle of a dental syringe.

U.S. Pat. No. 6,350,124, issued to Wade discloses a dental system comprising a hand piece having a housing and including a bur and air and water outlets for performing dental operations in an oral operating field; an inner cover separate from the housing having a shape substantially conforming to a shape of the hand piece for enclosing the hand piece and including a first aperture for receiving the bur and a second aperture for passing air and water from the air and water outlets of the hand piece; and an outer cover having a shape substantially conforming to a shape of the inner cover for enclosing the inner cover and including a first aperture for receiving the bur and a second aperture for passing air and water passed from the inner cover to the operating field.

A common drawback of the prior art barrier devices resides in the fact that the dental instrument is more difficult to grip and to manipulate after the barrier device has been interconnected with the dental instrument. This is generally because the ergonomics provided on the dental instrument are covered and masked by the barrier device. Another drawback of the prior art barrier devices concerns the difficulty in initially attaching the barrier device securely to the dental instrument and then the removal of the barrier device from the dental instrument following completion of the dental procedure.

It is the drawbacks of the prior art devices as set forth in the preceding paragraph that the protective barrier of the present invention seeks to overcome. As will be better understood from the discussion that follows, the protective barrier device of the present invention is very easy to connect and disconnect from dental instruments and like devices and uniquely replicates the ergonomic features found in the instrument. In one form of the invention the protective barrier device is fabricated from a moldable plastic that can be sterilized through use of appropriate antimicrobial liquids.

SUMMARY OF THE INVENTION

It is an object of the present invention to provide a unique protective barrier assemblage that can be removably fitted over a device to protect against the transfer of contaminants from one device to another.

Another object of the invention is to provide a protective barrier as described in the preceding paragraph which is of a novel design that enables the user to positively grip the device, as for example, a dental instrument during the conduct of dental procedures.

Another object of the invention is to provide a protective barrier assemblage of the aforementioned character which includes an inner sleeve and a spaced-apart outer sleeve which is connected to and cooperates with the inner sleeve to define a pair of hingably interconnected half portions, each of which has an elongated interior chamber filled with a yieldably deformable cushion material, such as a resilient, foamed polyurethane.

Another object of the invention is to provide a protective barrier assemblage as described in the preceding paragraph in which the surfaces of the inner sleeve of the protective barrier generally replicate the ergonomic features found on the outer surface of the dental instrument.

Another object of the invention is to provide a protective barrier of the class described in which the inner and outer sleeves are constructed from a moldable plastic that can be sterilized by soaking the protective barrier assemblage in an antimicrobial liquid.

Another object of the invention is to provide a protective barrier of the character described in the preceding paragraphs that is lightweight, durable and easy-to-use.

Another object of the invention is to provide a protective barrier that can be inexpensively fabricated in quantity using well-known plastic molding techniques.

DESCRIPTION OF THE INVENTION

Figure 1:
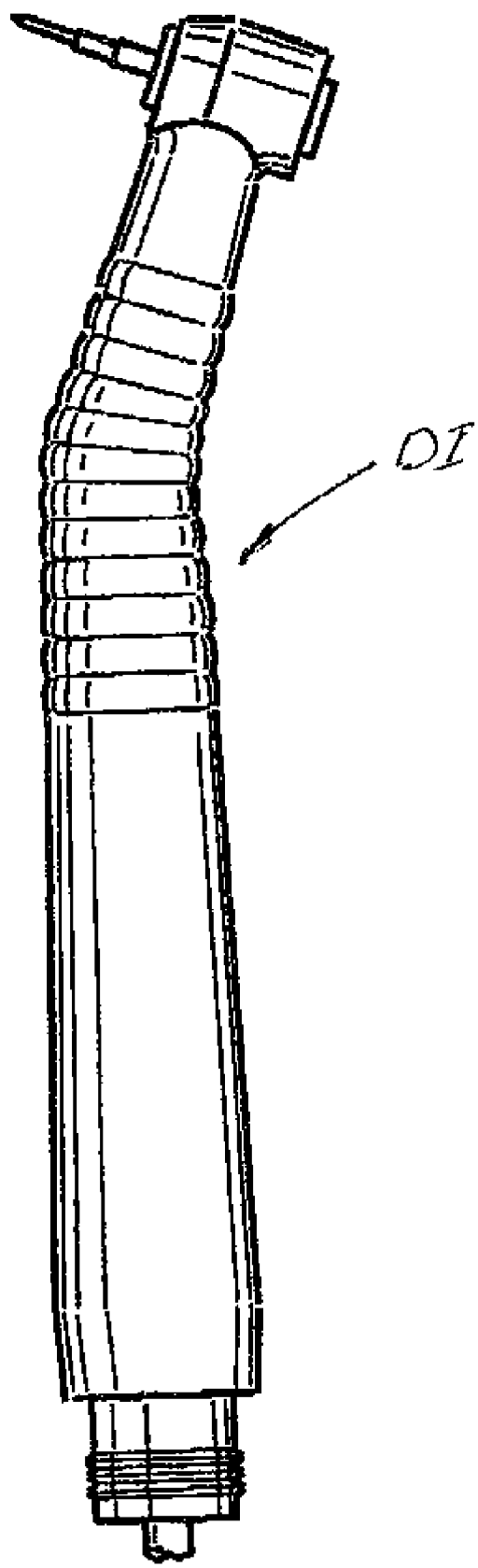
FIG. 1 is a generally perspective view of a prior art device with which the protective barrier of the invention can be used.
Figure 2:
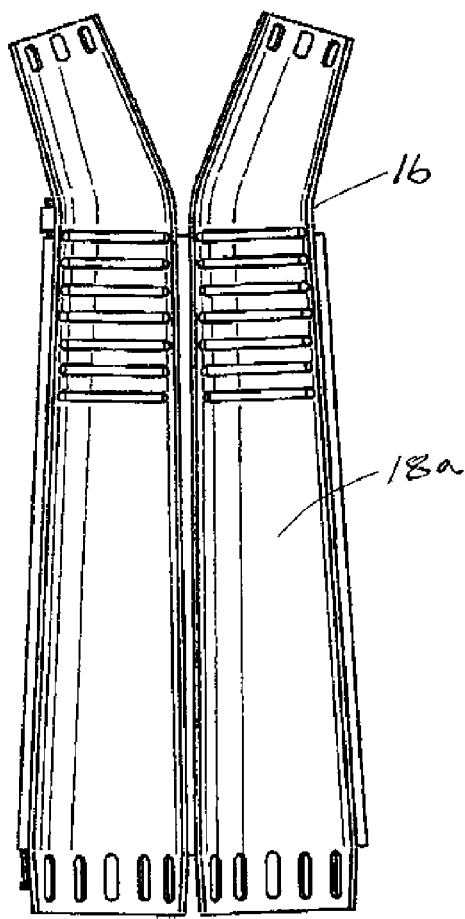
FIG. 2 is a plan view of the inner surface of the first, or inner sleeve of the protective barrier apparatus of one form of the invention.

Referring to the drawings and particularly to FIG. 1, one type of prior art dental instrument "DI" of the type with which the protective barrier device of the present invention can be used is there shown. It is to be understood that the type of dental instrument shown in FIG. 1 is merely exemplary of the many different types of dental instruments with which the barrier device of the present invention can be used.

Turning to FIGS. 2 through 8, one form of protective barrier device of the present invention is there shown for use in connection with a dental instrument "DI" of the character shown in FIG. 1. This protective barrier assemblage of the invention, which is generally designated by the numeral 14 (FIG. 4), is designed for placement over and in proximate contact with the outer surface of the handle portion of the dental instrument. However, it is to be understood that the protective barrier assemblage could also be constructed for placement over and in proximate contact with all or part of the dental instrument or in proximate contact with other types of hand-held instruments.

Figure 3:
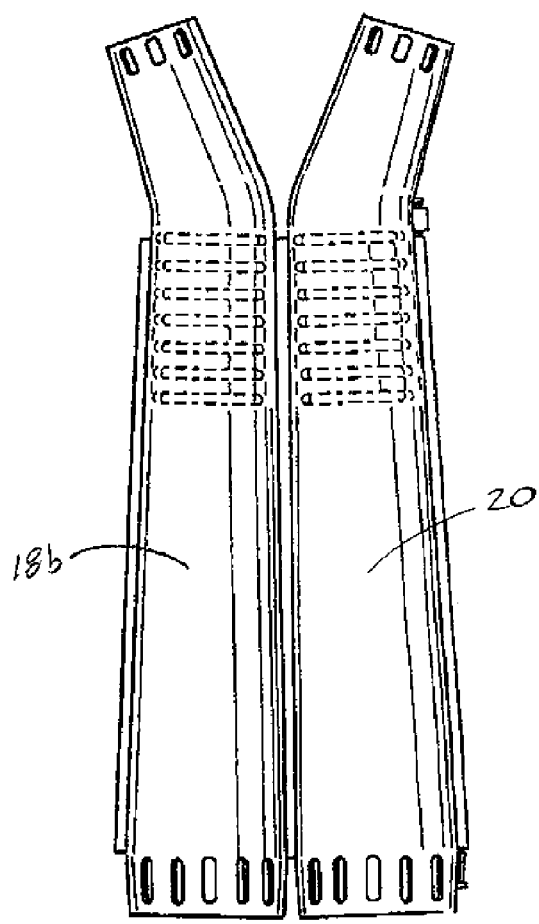
FIG. 3 is a plan view of the outer surface of the first, or inner sleeve of the protective barrier apparatus of one form of the invention.
Figure 8:
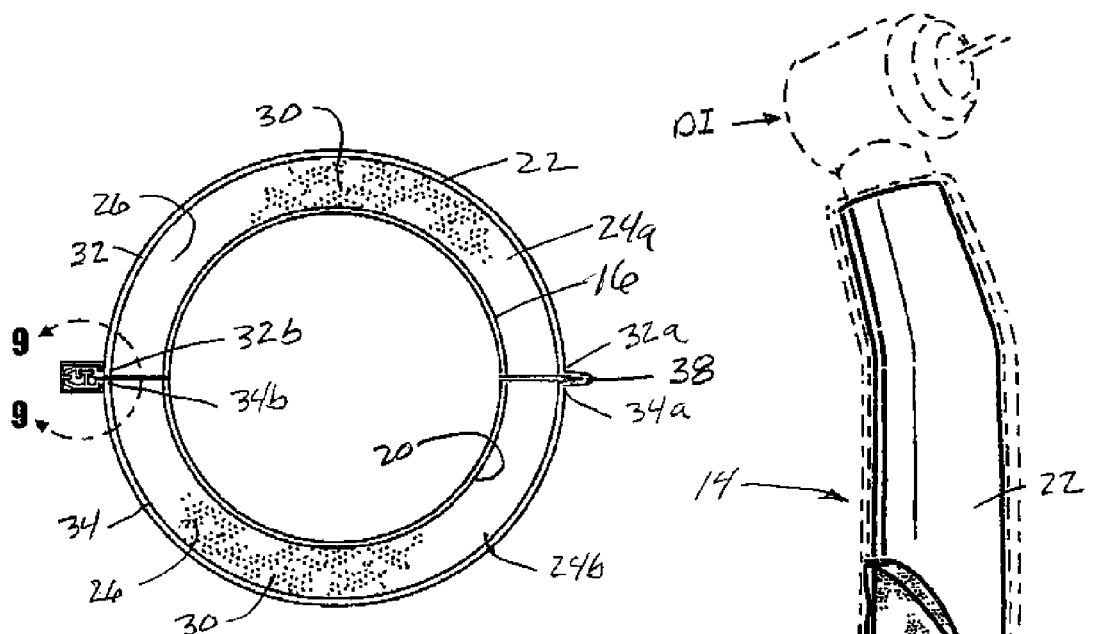
FIG. 8 is a cross-sectional view taken along lines 8—8 of FIG. 5.
Figure 6:
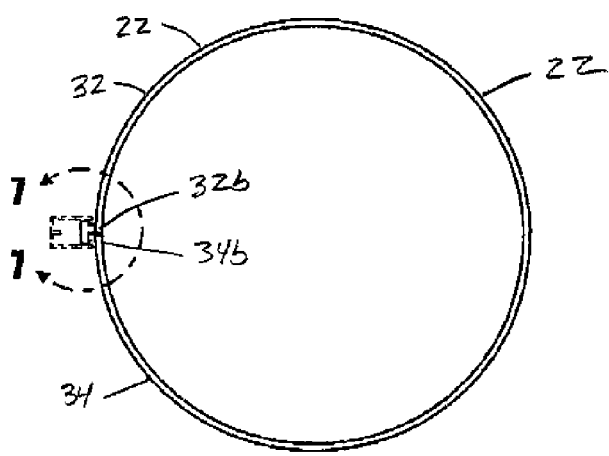
FIG. 6 is a cross-sectional view taken along line 6—6 of FIG. 5.

In the present embodiment of the invention the protective barrier assemblage 14 comprises a first substantially rigid inner plastic sleeve 16 having inner and outer surfaces 18a and 18b (FIGS. 2 and 3) which generally replicate at least a portion of the outer surface of the dental instrument "DI". As best seen in FIGS. 3 and 8, inner sleeve 16 also has a spaced-apart, outer surface 20.

A second, yieldably deformable, relatively thin plastic film outer sleeve 22 (FIG. 5) is connected to and cooperates with the first inner sleeve 16 to define a pair of the hingably interconnected half portions 24a and 24b (FIG. 8), each of which has an elongated interior chamber 26. Disposed within each elongated interior chamber 26 is a yieldably deformable cushion material 30. Yieldably deformable cushion material 30 can comprise various types of resilient foamed elastomer of a character well known to those skilled in the art. However, for present purposes, the yieldably deformable cushion material 30 preferably comprises a resilient foamed polyurethane. The resilient foamed elastomer, such as foamed polyurethane, can readily be molded to shape or cut to shape to fit within each elongated interior chamber 26.

Sleeves 16 and 22 can be of various thicknesses, but preferably have a thickness of between about 0.020 and about 0.1 inch. Construction of sleeve 16 is preferably accomplished by injection molding of a moldable plastic using an injection mold in which both sides of the mold cavity substantially replicate the outer surface of the dental instrument. In this regard, it is to be understood that the mold cavity is constructed so that the internal dimensions of sleeve 16 are slightly larger than the external dimension of the outer surfaces of the dental instrument. In this way some clearance is provided between of the protective barrier and the dental instrument.

Referring particularly to FIG. 8, it can be seen that second sleeve 22 comprises a first segment 32 having a first margin 32a and a second segment 34 having a first margin 34a. In the present form of the invention, first margin 32a of first segment 32 is connected to first margin 34a of second segment 34 by a living hinge 38 (see also FIG. 10) so that the two halves of the barrier assembly can be moved from the closed position shown in FIG. 8 to the open, dental instrument receiving position shown in FIG. 10.

Figures 9, 10:
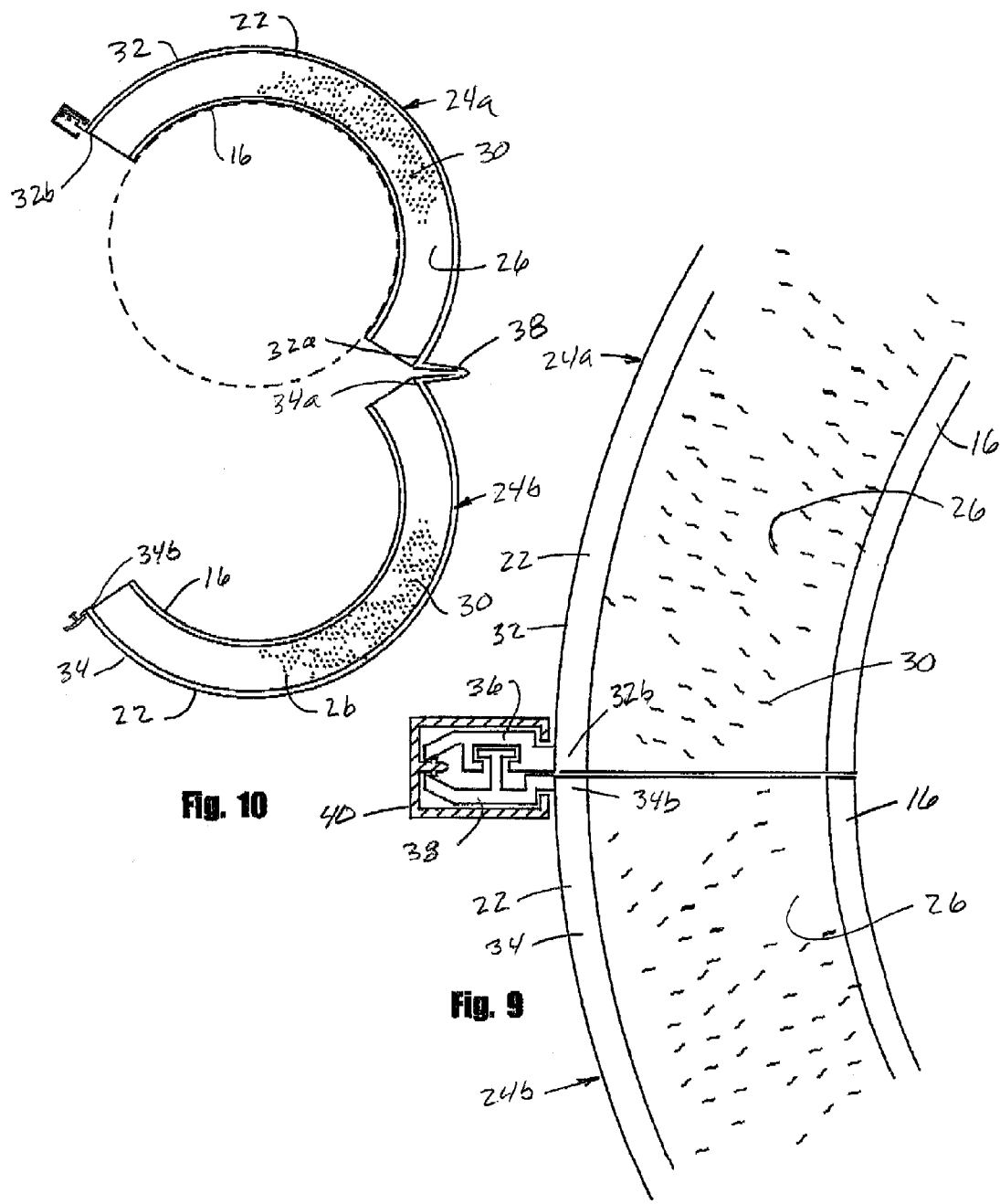
FIG. 9 is an enlarged fragmentary view of the area designated as 9—9 in FIG. 8.
FIG. 10 is a cross-sectional view similar to FIG. 8 but showing the two half portions of the protective barrier moved into an open position.

First segment 32 of second sleeve 22 also has a second margin 32b and second segment 34 of second sleeve 22 also has a second margin 34b. As illustrated in FIGS. 8 and 9, second margin 32b of first segment 32 is connected to second margin 34b of second segment 34 by connector means for releasably interconnecting together the first and second segments. The connector means of the present form of the invention comprises a conventional type of zipper, or "zip-lock" type arrangement. More particularly, as best seen in FIG. 9, second margins 32b and 34b have mating, strategically configured interlocking portions 36 and 38 respectively which can be interconnected and disconnected by a slider assembly 40 of conventional design which comprises a part of the connector means of the invention.

Figure 4:
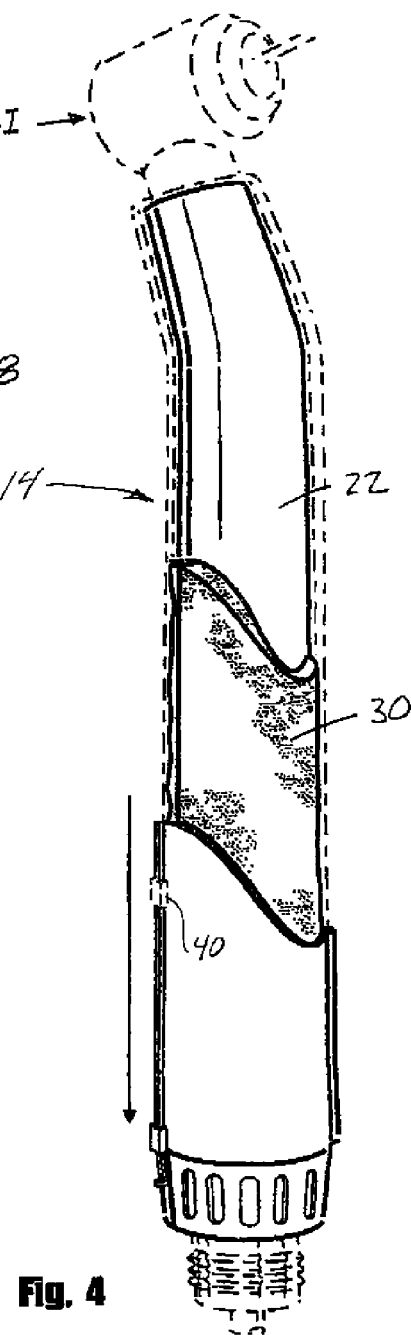
FIG. 4 is a generally perspective view of the assembled protective barrier of one form of the invention, partly broken away to show internal construction.
Figure 5:
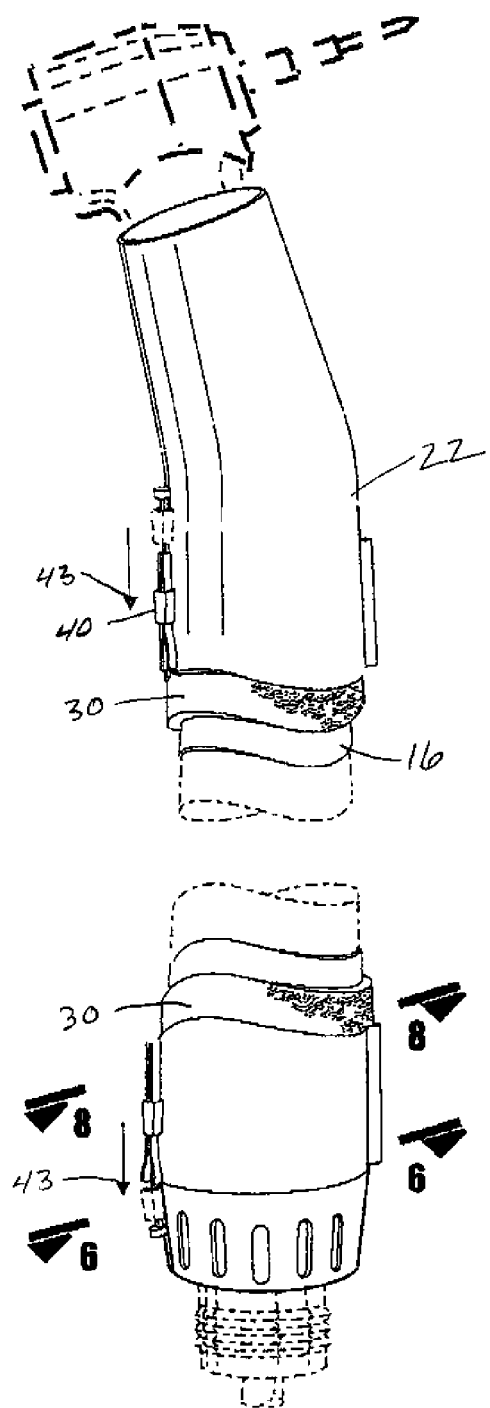
FIG. 5 is a generally perspective exploded view of the protective barrier shown in FIG. 4.
Figure 7:
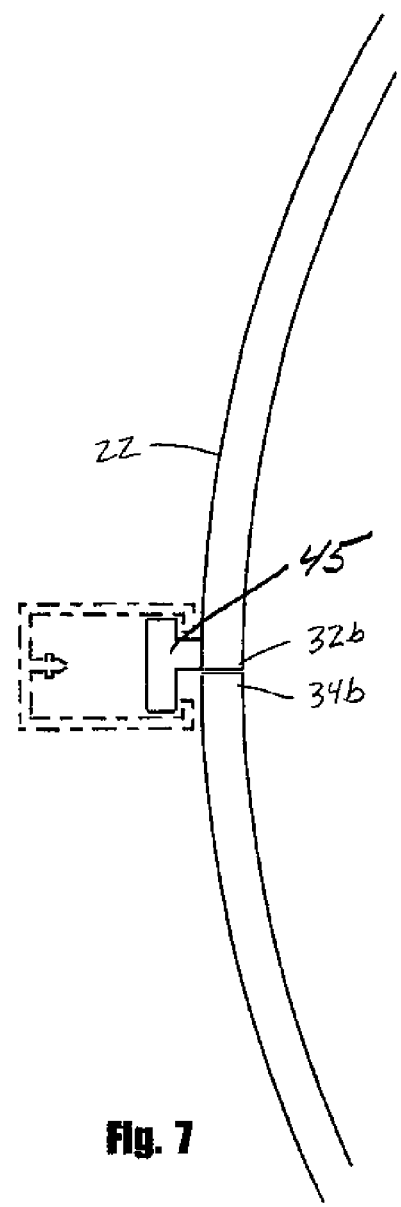
FIG. 7 is an enlarged fragmentary view of the area designated as 7—7 in FIG. 6.

As indicated in FIGS. 4, 5 and 8, slider assembly 40 is disposed for movement along the second margins of the first and second segments 32 and 34 of the second sleeve 22 in a manner to engage and disengage the mating interlocking portions 36 and 38. When the interlocking portions are interconnected by sliding the slider assembly downwardly of the assemblage as indicated by the arrows 43 in FIG. 5, the two halves of the barrier assembly are moved into the closed configuration shown in FIG. 8 to encase the handle portion of the dental instrument. Conversely, when the slider assembly is moved upwardly of the assemblage, the two halves of the assembly can be pivoted about the living hinge into the position shown in FIG. 10 so that the assemblage can be conveniently removed from the dental instrument. As illustrated in FIG. 7, a conventional zipper type end-stop 45 is interconnected with segment 32 of outer sleeve 22.

In using the barrier assembly of the present invention, the connector means are manipulated so as to permit the barrier assembly to be moved into the open configuration shown in FIG. 10. In this configuration, the handle portion of the dental instrument can be inserted into the open assembly as indicated by the dotted lines in FIG. 10. Once the handle of the dental instrument is in position within the barrier assembly, the two halves of the assembly can be closed and the connector means can be used to secure the assembly about the handle of the dental instrument.

Figure 11:
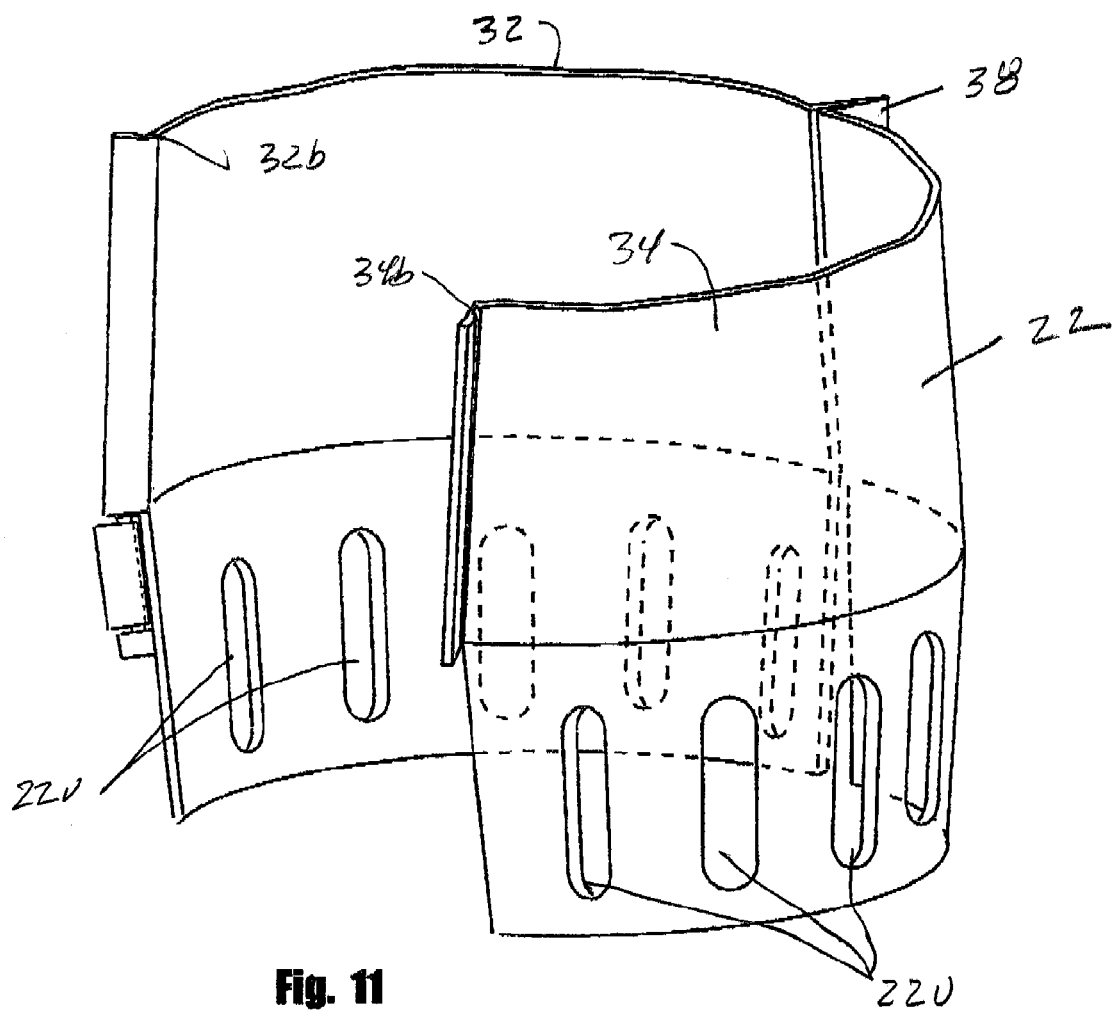
FIG. 11 is an enlarged fragmentary perspective view of the lower portion of the second, or outer sleeve of the protective barrier assemblage shown in FIG. 5.

With the barrier assembly in the closed configuration, when the caregiver grips the barrier assembly, the thin outer flexible sleeve portion 22 of the assembly will tend readily to conform to the caregiver's hand and fingers and will impart a deforming pressure to the yieldably deformable, cushion-like foam 30. The consistency of the foam 30 is such that it will readily conform to the shape of the deformed outer flexible sleeve portion and at the same time will also conform to the shape of the inner surface of the inner sleeve of the assembly which replicates the outer surface of the handle of the dental instrument. The net effect of this deformation of the outer sleeve 22 and the yieldably deformable, cushion like foam 30 permits the caregiver to securely grip the dental instrument and to provide substantially the same feel to the caregiver as would be experienced as a result of directly gripping the handle of the dental instrument itself. More particularly, because the ergonomic features provided on the dental instrument are replicated on the inner sleeve of the protective barrier and the cushion foam 30, upon being compressed, will closely conform to the outer surface of the inner sleeve, the caregiver can securely grip the protective barrier and readily manipulate it in the same manner as the dental instrument could be manipulated without the addition of the protective barrier. As indicated in FIG. 11 the lower extremity of sleeve 22 is provided with vent means here shown as a plurality of circumferentially-spaced vent openings 22v for permitting equalization of air pressure with the barrier assembly.

Upon the completion of the dental procedure, the connector means can be manipulated to once again permit the two halves of the barrier assembly to be moved into the open position shown in FIG. 10 of the drawings. In this position the dental instrument can be conveniently removed from the barrier assembly and the barrier assembly can either be discarded, or alternatively sterilized in an appropriate antimicrobial liquid.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following documents.

What is claimed is:

1. A protective barrier for placement over and in proximate contact with at least a portion of the outer surface of a device, said protective barrier comprising:
   (a) a first substantially rigid inner sleeve having an inner surface and a spaced-apart outer surface, said inner surface generally replicating at least a portion of the outer surface of the device;
   (b) a second, yieldably deformable outer sleeve connected to and spaced-apart from said first inner sleeve to define an elongated chamber between said first and second sleeves; and
   (c) a yieldably deformable cushion material disposed within said elongated chamber.

2. The protective barrier as defined in claim 1 in which said yieldably deformable cushion material comprises a resilient foamed elastomer.

3. The protective barrier as defined in claim 1 in which said yieldably deformable cushion material comprises a resilient foamed polyurethane.

4. The protective barrier as defined in claim 1 in which said second sleeve comprises a first segment having a first margin and a second segment having a first margin, said first margin of said first segment being connected to said first margin of said second segment by a living hinge.

5. The protective barrier as defined in claim 4 in which said first segment of said second sleeve has a second margin and in which said second segment of said second sleeve has a second margin, said second margin of said first segment being connected to said second margin of said second segment by connector means for releasably interconnecting said second margin of said first segment with said second margin of said second segment.

6. The protective barrier as defined in claim 5 in which said second margins of said first and second segments of said second sleeve have mating interlocking portions and in which said connector means comprises a slider disposed for movement along said second margins of said first and second segments of said second sleeve to engage and disengage said mating interlocking portions.

7. A protective barrier for placement over and in proximate contact with at least a portion of the outer surface of a dental instrument, said protective barrier comprising:
   (a) a first substantially rigid inner sleeve having an inner surface and a spaced-apart outer surface, said inner surface generally replicating at least a portion of the outer surface of the dental instrument;
   (b) a second, yieldably deformable outer sleeve connected to and cooperating with said first inner sleeve to define a pair of the hingably interconnected half portions, each said half portion having an elongated interior chamber;
   (c) a yieldably deformable cushion material disposed within said elongated interior chamber; and
   (d) connector means for releasably interconnecting said half portions.

8. The protective barrier as defined in claim 7 in which said yieldably deformable cushion material comprises a resilient foamed elastomer.

9. The protective barrier as defined in claim 7 in which said yieldably deformable cushion material comprises a resilient foamed polyurethane.

10. The protective barrier as defined in claim 7 in which said second sleeve comprises a first segment having a first margin and a second segment having a first margin, said first margin of said first segment being connected to said first margin of said second segment by a living hinge.

11. The protective barrier as defined in claim 10 in which said first segment of said second sleeve has a second margin and in which said second segment of said second sleeve has a second margin, said second margin of said first segment being connected to said second margin of said second segment by said connector means.

12. The protective barrier as defined in claim 11 in which said second margin of said first and second segments of said second sleeve have mating interlocking portions and in which said connector means comprises a slider disposed for movement along said second margins of said first and second segments of said second sleeve to engage and disengage said mating interlocking portions.

13. The protective barrier as defined in claim 11 in which said second sleeve includes vent means for venting to atmosphere any trapped gasses contained within the protective barrier.

14. The protective barrier as defined in claim 11 in which said first sleeve has a thickness of between about 0.020 and about 0.1 inch.

15. A protective barrier for placement over and in proximate contact with at least a portion of the outer surface of a dental instrument, said protective barrier comprising:
   (a) a first substantially rigid inner sleeve having an inner surface and a spaced-apart outer surface, said inner and outer surfaces generally replicating at least a portion of the outer surface of the dental instrument;
   (b) a second, yieldably deformable, thin plastic outer sleeve connected to and cooperating with said first inner sleeve to define a pair of the hingably interconnected half portions, each said half portion having an elongated interior chamber; and
   (c) a yieldably deformable cushion material disposed within said elongated interior chamber, said yieldably deformable cushion material comprising a resilient foamed polyurethane.

16. The protective barrier as defined in claim 15 in which said second sleeve comprises a first segment having a first margin and a second segment having a first margin, said first margin of said first segment being connected to said first margin of said second segment by a living hinge.

17. The protective barrier as defined in claim 16 in which said first segment of said second sleeve has a second margin and in which said second segment of said second sleeve has a second margin, said second margin of said first segment being connected to said second margin of said second segment by connector means for releasably interconnecting said second margin of said first segment with said second margin of said second segment.

18. The protective barrier as defined in claim 17 in which said second margin of said first and second segments of said second sleeve have mating interlocking portions and in which said connector means comprises a slider disposed for movement along said second margins of said first and second segments of said second sleeve to engage and disengage said mating interlocking portions.

19. The protective barrier as defined in claim 18 in which said second sleeve includes vent means for venting to atmosphere any trapped gasses contained within the protective barrier.

20. The protective barrier as defined in claim 19 in which said first sleeve has a thickness of between about 0.020 and about 0.1 inch.

* * * * *